United States Patent [19]

Grohe et al.

[11] Patent Number: 4,753,925

[45] Date of Patent: * Jun. 28, 1988

[54] ANTIBACTERIAL 1,7-DIAMINO-1,4-DIHYDRO-4-OXO-3-QUINOLINECARBOXYLIC ACIDS

[75] Inventors: Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[*] Notice: The portion of the term of this patent subsequent to May 19, 2004 has been disclaimed.

[21] Appl. No.: 899,458

[22] Filed: Aug. 22, 1986

Related U.S. Application Data

[62] Division of Ser. No. 712,490, Mar. 15, 1985, Pat. No. 4,666,920.

[30] Foreign Application Priority Data

Mar. 17, 1984 [DE] Fed. Rep. of Germany ....... 3409922

[51] Int. Cl.$^4$ .................. A61K 31/495; A61K 31/47; C07D 401/04
[52] U.S. Cl. .................................. 514/254; 514/313; 514/314; 514/235.2; 544/128; 544/363; 546/156
[58] Field of Search .................. 544/62, 128, 363; 546/156; 514/312, 222, 227, 254, 313, 314

[56] References Cited

U.S. PATENT DOCUMENTS

| 4,284,629 | 8/1981 | Grohe et al. | 544/363 |
| 4,398,029 | 8/1983 | Irikura | 544/128 |
| 4,499,091 | 2/1985 | Wentland | 514/312 |
| 4,530,930 | 7/1985 | Uno | 514/312 |

FOREIGN PATENT DOCUMENTS

| 0009425 | 4/1980 | European Pat. Off. |  |
| 27752 | 4/1981 | European Pat. Off. |  |
| 126355 | 11/1984 | European Pat. Off. |  |
| 40656 | 3/1980 | Japan | 514/312 |
| 2094305 | 9/1982 | United Kingdom. |  |

OTHER PUBLICATIONS

Antibiotics in Laboratory Medicine–2nd Edition Lorian.

*Primary Examiner*—Donald G. Daus
*Assistant Examiner*—Cecilia Shen
*Attorney, Agent, or Firm*—Sprung Horn Kramer & Woods

[57] ABSTRACT

Antibacterially effective 1,7-diamino-1,4-dihydro-4-oxo-3-(aza)quinolinecarboxylic acids of the formula

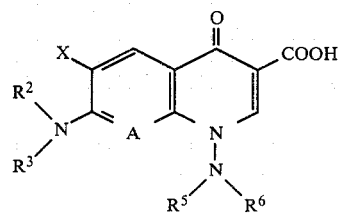

in which A is nitrogen or C—$R^1$, $R^1$ is nitro or halogen, $R^2$ and $R^3$ each independently is $C_1$–$C_3$-alkyl, or together with the nitrogen atom to which they are bonded, form a 5-membered or 6-membered heterocyclic ring, which can additionally contain the atoms or groups —O—, —S—, —SO—, —SO$_2$— or =N—$R^4$ as a ring member and can optionally be mono-, di- or tri-substituted on the carbon atoms by $C_1$–$C_3$-alkyl, hydroxyl, alkoxy with 1–3 carbon atoms, amino, methylamino or ethylamino, it being possible for a carbon atom in each case to carry only one substituent, $R^4$ is hydrogen, an alkyl or alkenyl group which has 1 to 4 carbon atoms and is optionally substituted by a hydroxyl, alkoxy, alkylmercapto, alkylamino or dialkylamino group with 1 to 3 carbon atoms per alkyl radical, the cyano group or an alkoxycarbonyl group with 1 to 4 carbon atoms in the alcohol part, or a benzyloxycarbonyl group.

11 Claims, No Drawings

ANTIBACTERIAL 1,7-DIAMINO-1,4-DIHYDRO-4-OXO-3-QUINOLINECARBOXYLIC ACIDS

This is a division of application Ser. No. 712,490, filed Mar. 15, 1985, now U.S. Pat. No. 4,666,920.

The present invention relates to new 1,7-diamino-1,4-dihydro-4-oxo-3-(aza)quinolinecarboxylic acids, a process for their preparation and their use in combating bacterial diseases.

It has been found that the new 1,7-diamino-1,4-dihydro-4-oxo-3-(aza)quinolinecarboxylic acids of the formula (I)

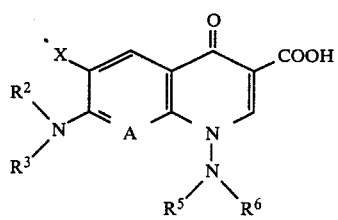

in which A can be nitrogen or C—$R^1$,
wherein
$R^1$ represents the nitro group or halogen, preferably fluorine,
$R^2$ and $R^3$ can be identical or different and represent a $C_1$–$C_3$-alkyl radical, or furthermore, together with the nitrogen atom to which they are bonded, can form a 5-membered or 6-membered heterocyclic ring, which can additionally contain the atoms or groups —O—, —S—, —SO—, —SO$_2$— or N—$R^4$ as a ring member and can optionally be mono-, di- or tri-substituted on the carbon atoms by $C_1$–$C_3$-alkyl, hydroxyl, alkoxy with 1–3 carbon atoms, amino, methylamino or ethylamino, it being possible for a carbon atom in each case to carry only one substituent, wherein
$R^4$ represents hydrogen, a branched or straight-chain alkyl or alkenyl group which has 1 to 4 carbon atoms and can optionally be substituted by a hydroxyl, alkoxy, alkylmercapto, alkylamino or dialkylamino group with 1 to 3 carbon atoms in each alkyl radical, the cyano group or the alkoxycarbonyl group with 1 to 4 carbon atoms in the alcohol part, or the benzyloxycarbonyl group, a phenylalkyl group which has up to 4 carbon atoms in the aliphatic part and is optionally substituted in the phenyl radical, a phenyl radical which is optionally monosubstituted or disubstituted by hydroxyl, methoxy, chlorine and fluorine, a phenylacyl radical which is optionally monosubstituted or disubstituted by hydroxyl, methoxy, chlorine or fluorine, an oxoalkyl radical with up to 6 carbon atoms or a cycloalkyl-alkyl radical which has up to 6 carbon atoms in the cyclic part and up to 3 carbon atoms in the acyclic part,
$R^5$ and $R^6$ can be identical or different and denote hydrogen or an alkyl group with 1 to 4 carbon atoms, and furthermore
X represents hydrogen, the nitro group or halogen, preferably fluorine or chlorine,
and pharmaceutically useful salts thereof, are suitable as antibacterial active compounds for human medicine and veterinary medicine, veterinary medicine also including prophylaxis and treatment of fish.

Preferred compounds of the formula (I) are those in which
X and $R^1$ represent halogen, preferably fluorine or chlorine, and
$R^2$, $R^3$, $R^4$, $R^5$ and $R^6$ have the abovementioned meaning.

Particularly preferred compounds of the formula (I) are those in which A can be nitrogen or C—$R^1$, wherein
$R^1$ represents a nitro group, and
X, $R^2$, $R^3$, $R^4$, $R^5$ and $R^6$ have the abovementioned meaning.

It has furthermore been found that 1,7-diamino-1,4-dihydro-4-oxo-3-(aza)quinolinecarboxylic acids of the formula (I) are obtained by a process in which the 1-aminoquinolinecarboxylic acids of the formula (II)

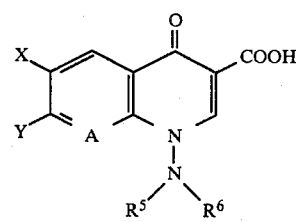

in which
X, A, $R^5$ and $R^6$ have the abovementioned meaning and Y represents halogen, preferably chlorine or fluorine, are reacted with amines of the formula (III)

in which $R^2$ and $R^3$ have the abovementioned meaning, if appropriate in the presence of acid-binding agents.

If piperazine and 1-amino-6,7,8-trifluoro-1,4-dihydro-4-oxo-3-quinolinecarboxylic acid are used as the starting substances for the reaction, the course of the reaction can be represented by the following equation:

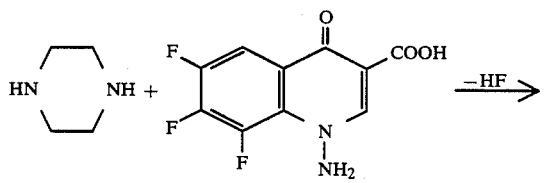

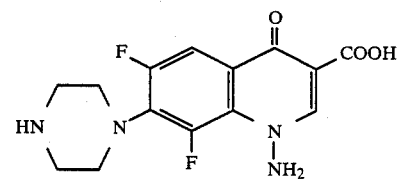

The 1-aminoquinolinecarboxylic acids of the formula (II) which can be used as starting substances can be prepared according to the following equation:

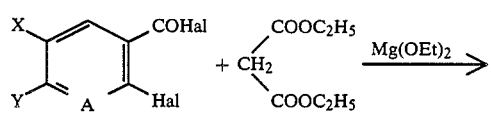

(1)           (2)

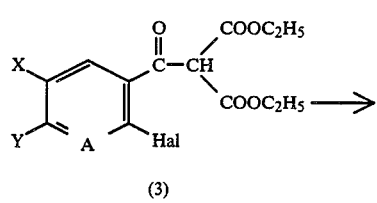

(3)

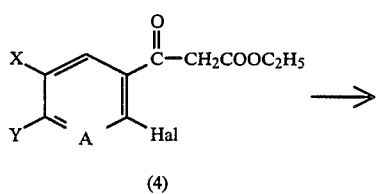

(4)

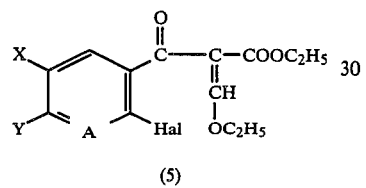

(5)

In this reaction, diethylmalonate (2) is acylated with the o-halogenoaroyl halides (1) in the presence of magnesium ethylate to give the aroylmalonic acid esters (3) (Organicum, 3rd edition, 1964, page 438). A good yield of the aroylacetic acid ethyl esters (4) is obtained by partial hydrolysis and decarboxylation of (3) in an aqueous medium with catalytic amounts of sulphuric acid or p-toluenesulphonic acid, and these products are converted into the 2-aroyl-3-ethoxy-acrylic acid ethyl esters (5) with triethyl o-formate/acetic anhydride.

(a) The reaction of (5) with 1,1-dialkylhydrazines (6) ($R^5$ and $R^6 = C_1-C_4$-alkyl) leads to the 2-aroyl-3-hydrazino-acrylic acid esters (7). The exothermic reaction is carried out in a solvent, such as, for example, ethanol, methylene chloride or toluene.

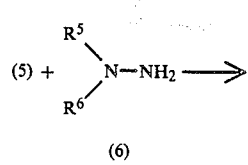

(6)

($R^5$, $R^6 = C_1-C_4$—Alkyl)

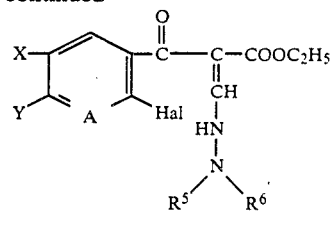

(7)

($R^5$ and $R^6 = C_1-C_4$—alkyl)

(b) (5) gives the 2-aroyl-3-hydrazino-acrylic acid esters (9) with 1-alkyl-1-acyl-hydrazines (8).

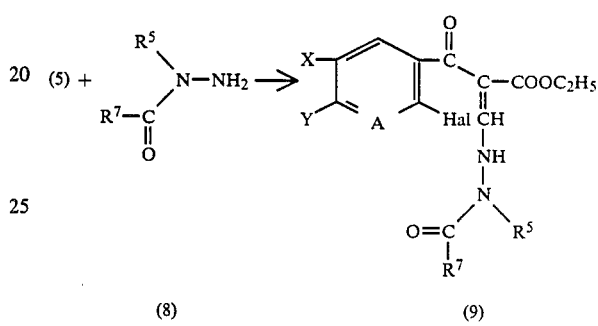

(8)           (9)

In this equation,
$R^5$ represents $C_1-C_4$-alkyl and
$R^7$ represents hydrogen, alkyl with 1-3 carbon atoms, phenyl or alkoxy with 1-3 carbon atoms.

(c) Finally, the hydrazones (10) are converted into the enhydrazines 11 with (5).

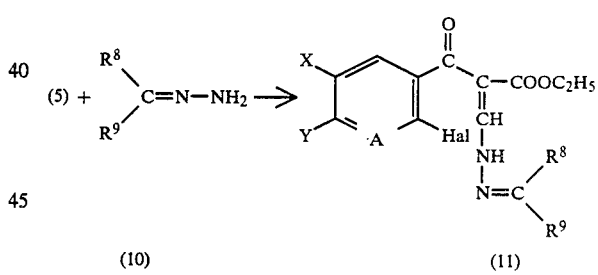

(10)           (11)

$R^8$ can denote hydrogen, $C_1-C_3$-alkyl or phenyl and $R^9$ can denote $C_1-C_3$-alkyl or phenyl.

The 2-aroyl-3-hydrazino-acrylic acid esters (7), (9) and (11) are cyclized to the substituted 1-amino-(aza)-quinolonecarboxylic acid esters (12), (13) and (14), if appropriate in the presence of a diluent and an acid-binding agent in a temperature range of about 60°–300° C., preferably 80°–180° C.

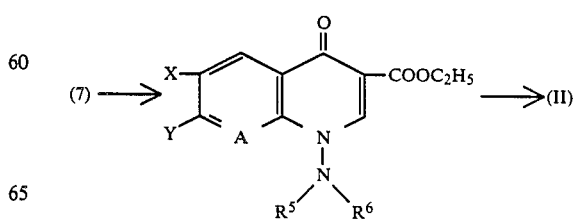

(12)

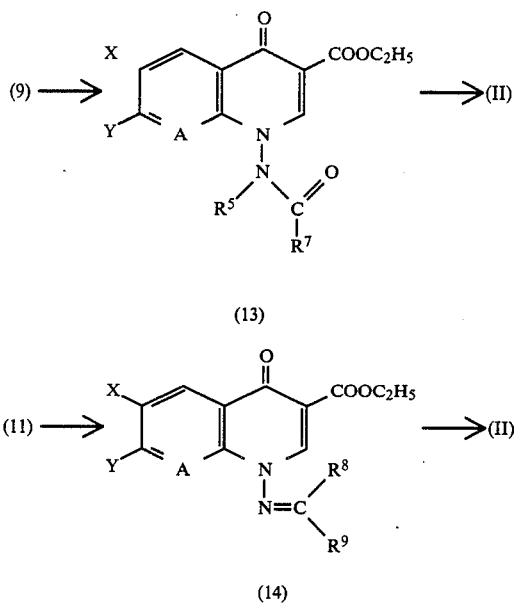

Diluents which can be used are toluene, dioxane, dimethylsulphoxide, N-methylpyrrolidone, sulpholane, hexamethylphosphoric acid triamide and N,N-dimethylformamide.

Possible acid-binding agents for this reaction stage are potassium tert.-butanolate, butyl-lithium, lithiumphenyl, sodium methylate, sodium hydride, sodium carbonate, potassium carbonate, DBU (1,8-diazabicyclo[5.4.0]undec-7-ene) and, if the halogen atom in the 2-position of the aroyl radical in (7), (9) or (11) is fluorine, preferably potassium fluoride or sodium fluoride. It may be advantageous to use an excess of 5mol% of base.

The ester hydrolysis of (12) which takes place in the last step under basic or acid conditions leads to the (aza)quinolonecarboxylic acids (II) ($R^5$ and $R^6 = C_1-C_4$-alkyl).

In the reaction of the 1-acylamino-quinolonecarboxylic acid ester (13) with 2 equivalents of alkali metal hydroxide solution, the acyl radical is split off and the ester group is hydrolyzed. The corresponding (aza)quinolonecarboxylic acids II ($R^5 = H$, $R^6 = C_1-C_4$-alkyl) are obtained in a good yield.

If the radicals $R^8$ and $R^9$ of the hydrazone ester (14) represent, for example, a methyl group, splitting to give the 1-amino-(aza)quinolonecarboxylic acid esters and acetone can be carried out in the presence of 1 mole of $H_2O$ and catalytic amounts of p-toluenesulphonic acid. The acetone is thereby distilled out of the equilibrium with isopropanol. The 1-amino-(aza)quinolonecarboxylic acid esters are then hydrolyzed under alkaline conditions to give the corresponding (aza)quinolonecarboxylic acids (II) ($R^5 = R^6 = H$).

The o-halogeno-(het)aroyl halides (1) used as starting substances are known, or they can be obtained by processes which are known from the literature. Examples which may be mentioned are: 2,6-dichloro-nicotinic acid chloride (F. Mutterer and C. D. Weis, *Helv. Chim. Acta* 59, 222 (1976).

2,3,4,5-Tetrafluorobenzoyl chloride and 2,4,5-trifluorobenzoyl chloride have been obtained from 2,3,4,5-tetrafluoro-benzoic acid, which is known from the literature (G. G. Yakobsen, V. N. Odinokov and N. N. Vorozhtsov Jr., *Zh. Obsh. Khim.* 36, (1966), and 2,4,5-trifluoro-benzoic acid, which is known from the literature (J. I. DeGraw, M. Cory and W. A. Skinner, *J. Chem. Eng. Data* 13, 587 (1986)) with thionyl chloride in the customary manner. 2,3,4,5-Tetrafluorobenzoyl chloride has a boiling point of 75°–80°C./17 mbar. 2,4,5-Trifluorobenzoyl chloride has a boiling point of 82°–84° C./13 mbar.

2,4-Dichloro-5-fluoro-3-nitrobenzoyl chloride has been obtained by nitration of 2,4-dichloro-5-fluorobenzoic acid to give 2,4-dichloro-5-fluoro-3-nitrobenzoic acid and reaction thereof with thionyl chloride.

The amines (III) used as starting substances are known, or they can be obtained by processes which are known from the literature. Examples which may be mentioned are: piperidine, morpholine, pyrrolidine, dimethylamine, piperazine, 1-methylpiperazine, 1-ethylpiperazine, 1-β-hydroxyethylpiperazine, 1-formylpiperazine, 2-methylpiperazine, 1,2-dimethylpiperazine, 2-ethylpiperazine and 2-propylpiperazine.

The hydrazine derivatives (6), (8) and (10) used as starting substances are likewise known, or they can be prepared by processes which are known from the literature.

Examples which may be mentioned are: dimethylhydrazine, diethylhydrazine, di-n-butylhydrazine, 1-formyl-1-methylhydrazine, 1-formyl-1-ethylhydrazine, 1-formyl-1-n-butylhydrazine, 1-acetyl-1-methylhydrazine, 1-acetyl-1-ethylhydrazine, 1-benzoyl-1-methylhydrazine, 1-ethoxycarbonyl-1-methylhydrazine, acetone hydrazone, benzaldehyde hydrazone, acetophenone hydrazone, benzophenone hydrazone and methyl ethyl ketone hydrazone.

The reaction of (II) with (III) is preferably carried out in a diluent, such as dimethylsulphoxide, N,N-dimethylformamide, hexamethylphosphoric acid triamide, sulpholane, water, an alcohol, such as methanol, ethanol, n-propanol or isopropanol, glycol monomethyl ether or pyridine. Mixtures of these diluents can also be used.

All the usual inorganic and organic acid-binding agents can be used as the acid-binding agents. These include, preferably, the alkali metal hydroxides, alkali metal carbonates, organic amines and amidines. Specific agents which may be mentioned as particularly suitable are: triethylamine, 1,4-diazabicyclo[2,2,2]-octane (DABCO), excess amine (III) or 1,8-diazabicyclo[5,4,-0]undec-7-ene (DBU).

The reaction temperatures can be varied within a substantial range. In general, the reaction is carried out between about 0° and 200° C., preferably between 20° and 160° C.

The reaction can be carried out under normal pressure or under increased pressure. In general, the reaction is carried out under pressures of between about 1 and about 100 bar, preferably between 1 and 10 bar.

In carrying out the process according to the invention, 1 to 15 moles, preferably 1 to 6 moles, of the amine (III) are employed per mole of carboxylic acid (II).

New active compounds which may be mentioned specifically are: 1-amino-6,8-difluoro-1,4-dihydro-4-oxo-7-(1-piperazinyl)-3-qniolinecarboxylic acid, 1-amino-6,8-difluoro-1,4-dihydro-4-oxo-7-(4-methyl-1-piperazinyl)-3-quinolinecarboxylic acid, 1-amino-6,8-difluoro-1,4-dihydro-4-oxo-7-(4-ethyl-1-piperazinyl)-3-quinolinecarboxylic acid, 1-amino-6,8-difluoro-1,4-dihydro-4-oxo-7-(3-methyl-1-piperazinyl)-3- quinolinecarboxylic acid, 1-amino-6,8-difluoro-1,4-dihydro-4-oxo-(3,4-dimethyl-1-piperazinyl)-3-quinolinecarboxylic acid, 1-methylamino-6,8-difluoro-1,4-dihydro-4-oxo-7-(1-piperazinyl)-3-quinolinecarboxylic acid, 1-methylamino-6,8-difluoro-1,4-dihydro-4-oxo-7-(4-methyl-1-piperazinyl)-quinolinecarboxylic acid, 1-methylamino-6,8-difluoro-1,4-dihydro-4-oxo-7-(4-ethyl-1-piperazinyl)-3-quinolinecarboxylic acid, 1-dimethylamino-6,8-difluoro-1,4-dihydro-4-oxo-7-(1-piperazinyl)-3-quinolinecarboxylic acid, 1-dimethylamino-6,8-difluoro-1,4-dihydro-4-oxo-7-(4-methyl-1-piperazinyl)-3-quinolinecarboxylic acid, 1-dimethylamino-6-fluoro-8-nitro-1,4-dihydro-4-oxo-7-(1-pyrrolidinyl)-3-quinolinecarboxylic acid, 1-dimethylamino-6-fluoro-8-nitro-1,4-dihydro-4-oxo-7-(1-piperazinyl)-3-quinolinecarboxylic acid, 1-dimethylamino-6-fluoro-8-nitro-1,4-dihydro-4-oxo-7-(4-methyl-1-piperazinyl)-3-quinolinecarboxylic acid, 1-methylamino-6-fluoro-8-nitro-1,4-dihydro-4-oxo-7-(1-piperazinyl)-3-quinolinecarboxylic acid, 1-methylamino-6-fluoro-8-nitro-1,4-dihydro-4-oxo-7-(4-methyl-1-piperazinyl)-3-quinolinecarboxylic acid, 1-amino-6-fluoro-8-nitro-1,4-dihydro-4-oxo-7-(1-piperazinyl)-3-quinolinecarboxylic acid and 1-amino-6-fluoro-8-nitro-1,4-dihydro-4-oxo-7-(4-methyl-1-piperazinyl)-3-quinolinecarboxylic acid, and their pharmaceutically useful acid addition salts, alkali metal salts, alkaline earth metal salts or hydrates.

PREPARATION EXAMPLES FOR THE STARTING SUBSTANCES

Example A

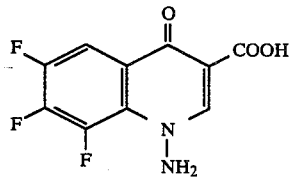

First 2.8 g of hydrazine hydrate and, 30 minutes later, 12.8 g of acetone are added dropwise to a solution of 16 g of ethyl 2-(2,3,4,5-tetrafluorobenzoyl)-3-ethoxyacrylate in 70 ml of ethanol, while cooling with dry ice/acetone at −25° C. to −30° C. The mixture is allowed to come slowly to room temperature and is then stirred at 20° C. to 25° C. for a further hour. The solvent is then distilled off in vacuo and the orange-colored residue is recrystallized from cyclohexane/light petrol. 12.5 g of ethyl 2-(2,3,4,5-tetrafluorobenzoyl)-3-(2-propylidenehydrazino)acrylate of melting point 86° C. are obtained.

10.38 g of ethyl 2-(2,3,4,5-tetrafluorobenzoyl)-3-(2-propylidenehydrazino)-acrylate, 2 g of sodium fluoride and 60 ml of dimethylformamide are heated at 150°–160° C. for 2.5 hours. The dimethylformamide is stripped off in vacuo, the residue is taken up in CH₂Cl₂/H₂O and the CH₂Cl phase is concentrated in vacuo, after drying with Na₂SO₄. Recrystallization from ethanol gives 6 g of ethyl 6,7,8-trifluoro-1-(2-propylideneamino)-1,4-dihydro-4-oxo-3-quinolinecarboxylate of melting point 166° C. A suspension of 6 g of the propyldeneamino-quinolinecarboxylic acid ester in 72 ml of isopropanol and 0.7 g of water is heated at 70° C. with 0.16 g of p-toluenesulphonic acid for 1 hour. About 50 ml are then distilled off under normal pressure, and 25 ml of water are added to the residue. The solid is filtered off with suction in the cold and rinsed with an isopropanol/water (1:1) mixture. 4.7 g of ethyl 1-amino-6,7,8-trifluoro-1,4-dihydro-4-oxo-3-quinolinecarboxylate of melting point 217° C. are obtained.

5.7 g of the ethyl 1-amino-quinolinecarboxylate are refluxed with 1.25 g of potassium hydroxide and 100 ml of water for 2.5 hours. The warm solution is filtered and the residue is rinsed with water. The filtrate is acidified to pH 1–2 with half-concentrated hydrochloric acid, while cooling with ice, and the precipitate is filtered off with suction, washed with water and dried at 100° C. in vacuo. After recrystallization from acetonitrile, 4 g of 1-amino-6,7,8-trifluoro-1,4-dihydro-4-oxo-3-quinolinecarboxylic acid of melting point 225°–226° C. are obtained.

PREPARATION OF THE STARTING SUSBTANCE 20.1 g of magnesium chips are suspended in 40 ml of anhydrous ethanol. 4 ml of carbon tetrachloride are added and, when the reaction has started, a mixture of 132.2 g of diethyl malonate, 80 ml of absolute ethanol and 320 ml of anhydrous toluene are added dropwise at 50°–60° C. When the reaction has subsided, the mixture is heated at 60° C. for a further 2 hours and cooled to −5° C. to −10° C. with dry ice/acetone, and a solution of 175.5 g of 2,3,4,5-tetrafluorobenzoyl chloride in 100 ml of absolute toluene is slowly added dropwise at this temperature. The mixture is stirred at 0° C. to −5° C. for 1 hour and is allowed to come to room temperature overnight, and a mixture of 350 ml of ice-wter and 50 ml of concentrated sulphuric acid is run in, while cooling with ice. The phases are separated and the aqueous phase is after-extracted twice with toluene. The combined toluene solutions are washed with saturated sodium chloride solution, and dried with sodium sulphate and the solvent is stripped off in vacuo. 284.8 g of diethyl 2,3,4,5-tetrafluoro-benzoyl-malonate are obtained as the crude product.

0.3 g of p-toluenesulphonic acid is added to an emulsion of 284.8 g of crude diethyl 2,3,4,5-tetrafluorobenzoyl-malonate in 300 ml of water. The mixture is heated at the boiling point for 4.5 hours, with thorough stirring, the cooled emulsion is extracted several times with methylene chloride, the combined methylene chloride solutions are washed once with saturated sodium chloride solution and dried with sodium sulphate and the solvent is distilled off in vacuo. Fractionation of the residue under a fine vacuum gives 160.2 g of ethyl 2,3,4,5-tetrafluorobenzoylacetate of boiling point 75°–96° C./0.06–0.09 mbar.

A mixture of 110.75 g of ethyl 2,3,4,5-tetrafluorobenzoylacetate, 93.5 g of ethyl o-formate and 107 g of acetic anhydride is heated at 150° C. for 2 hours. The volatile constituents are then distilled off under a water pump vacuum and finally under a fine vacuum at a bath temperature of 120° C. 123.9 g of crude ethyl 2,3,4,5-tetrafluorobenzoyl-3-ethoxy-acrylate remain. The product is sufficiently pure for the subsequent reactions.

Example B

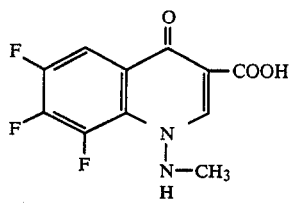

3.8 g of 1-formyl-1-methylhydrazine are added dropwise to a solution of 16 g of ethyl 2-(2,3,4,5-tetrafluorobenzoyl)-3-ethoxy-acrylate in 60 ml of ethanol, while cooling with ice and stirring. The mixture is stirred at room temperature for 1 hour, 60 ml of water are added, the mixture is cooled with ice and the precipitate is filtered off with suction and washed with water-/ethanol (1:1). 12 g of ethyl 2-(2,3,4,5-tetrafluorobenzoyl)-3-(2-formyl-2-methylhydrazino)-acrylate of melting point 92° C. are obtained.

12 g of the above compound are heated at 160° C. with 2.2 g of sodium fluoride and 100 ml of dimethylformamide for 2 hours. The mixture is poured onto 400 ml of ice-water and the solid is filtered off with suction, rinsed with $H_2O$ and dried at 100° C. in vacuo. 9.8 g of ethyl 6,7,8-trifluoro-1-(formylmethylamino)-1,4-dihydro-4-oxo-3-quinolinecarboxylate of melting point 185° C. are obtained.

A mixture of 9.6 g of the ethyl formyl-methylaminoquinolinecarboxylate, 150 ml of ethanol, 0.8 ml of $H_2O$ and 4.1 ml of triethylamine is heated at the boiling point under reflux for 2 hours. 150 ml of ice-water are then added and the precipitate is filtered off with suction and washed with ethanol/$H_2O$ (1:1). 7.5 g of ethyl 6,7,8-trifluoro-1-methylamino-1,4-dihydro-4-oxo-3-quinolinecarboxylate of melting point 189° C. are obtained.

7.5 g of the 1-methylamino-3-quinolinecarboxylic acid ester, 55 ml of glacial acetic acid, 40 ml of water and 6 ml of concentrated sulphuric acid are refluxed for 2 hours. The cooled solution is poured onto ice and the precipitate is filtered off with suction, washed with water and dried at 100° C. in vacuo. After recrystallization from dimethylformamide/ethanol, 4.8 g of 6,7,8-trifluoro-1-methylamino-1,4,-dihydro-4-oxo-quinolinecarboxylic acid of melting point 240° C. are obtained.

Example C

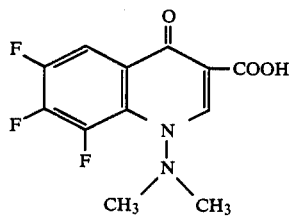

3.1 g of 1,1-dimethylhydrazine are added dropwise to a solution of 16 g of ethyl 2-(2,3,4,5-tetrafluorobenzoyl)-3-ethoxy-acrylate in 60 ml of ethanol, while cooling with ice and stirring. The mixture is stirred at room temperature for 1 hour, 60 ml of $H_2O$ are added, the mixture is cooled with ice and the precipitate is filtered off with suction and washed with water/ethanol (1:1). 12.9 g of ethyl 2-(2,3,4,5-tetrafluorobenzoyl)-3-(2,2-dimethylhydrazino)-acrylate of melting point 81° C. are obtained.

12.9 g of the above compound are heated at 160° C. with 2.5 g of sodium fluoride and 100 ml of dimethylformamide for 2 hours. The mixture is poured onto 400 ml of ice-water and the solid is filtered off with suction, rinsed with water and dried at 100° C. in vacuo. 11.4 g of ethyl 6,7,8-trifluoro-1-dimethylamino-1,4-dihydro-4-oxo-3-quinolinecarboxylate of melting point 172° C. are obtained.

11.2 g of the 1-dimethylamino-3-quinolinecarboxylic acid ester, 70 ml of glacial acetic acid, 55 ml of water and 7.8 ml of concentrated sulphuric acid are refluxed for 2 hours. The cooled solution is poured onto ice and the precipitate is filtered off with suction, washed with water and dried in vacuo at 100° C. After recrystallization from dimethylformamide/ethanol, 8.5 g of 6,7,8-trifluoro-1-dimethylamino-1,4-dihydro-4-oxo-3-quinolinecarboxylic acid of decomposition point 293°–295° C. are obtained.

The following compound can be prepared analogously to Examples A–C:

Example D

1-Methylamino-7-chloro-6-fluoro-8-nitro-1,4-dihydro-4-oxo-3-quinolinecarboxylic acid of decomposition point 270°–272° C.

PREPARATION EXAMPLES FOR THE END PRODUCTS ACCORDING TO THE INVENTION

Example 1

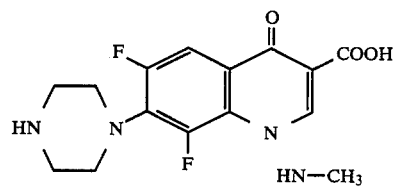

A mixture of 1.95 g of 1-methylamino-6,7,8-trifluoro-1,4-dihydro-4-oxo-3-quinolinecarboxylic acid, 3.05 g of anhydrous piperazine and 20 ml of dry pyridine is refluxed for 6 hours. The solvent is stripped off in vacuo, the residue is taken up in 20 ml of water, the pH is brought to 7-8 with half-concentrated hydrochloric acid, with cooling, and the precipitate is filtered off with suction, washed with ice-water and dried at 100° C. in vacuo. 1.8 g of 1-methylamino-6,8-difluoro-7-(1-piperazinyl)-1,4-dihydro-4-oxo-3-quinolinecarboxylic acid of decomposition point 276°–278° C. are obtained.

The following compounds are obtained analogously to Example 1:

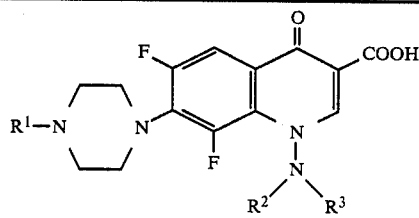

| Example | $R^1$ | $R^2$ | $R^3$ | Decomposition point (°C.) |
|---|---|---|---|---|
| 2 | $CH_3$ | $CH_3$ | $CH_3$ | 246 |
| 3 | $CH_3$ | H | $CH_3$ | 125 |

-continued

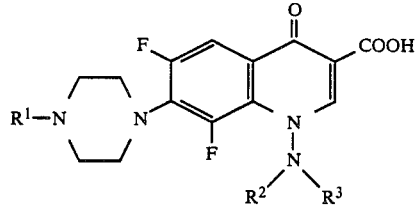

| Example | R¹ | R² | R³ | Decomposition point (°C.) |
|---------|----|----|----|---------------------------|
| 4 | H | H | H | 286 |

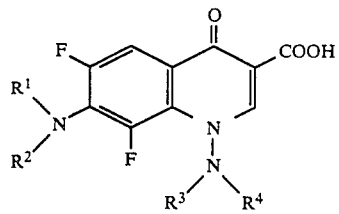

| Example | R¹ | R² | R³ | R⁴ | Decomposition point (°C.) |
|---------|----|----|----|----|--------------------------|
| 7 | —CH₂CH₂CH₂CH₂— | | H | H | 274 |
| 8 | —CH₂CH₂CH₂CH₂— | | CH₃ | CH₃ | 279 |
| 9 | —CH₂CH₂OCH₂CH₂— | | CH₃ | CH₃ | 284 |
| 10 | —CH₂CH₂OCH₂CH₂— | | H | H | 262 |

Example 5

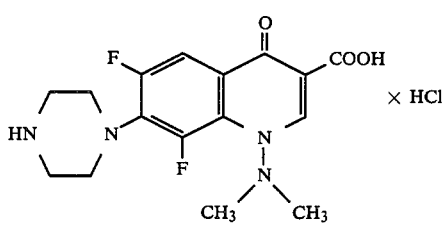

A mixture of 2.86 g of 1-dimethylamino-6,7,8-trifluoro-1,4-dihydro-4-oxo-3-quinolinecarboxylic acid, 4.3 g of anhydrous piperazine and 30 ml of dry pyridine is heated at the boiling point under reflux for 6 hours. The pyridine is then stripped off in vacuo and 10 ml of water are added to the residue. The pH of the solution is brought to about 1 with concentrated hydrochloric acid and the precipitate is filtered off with suction in the cold and washed with a little ice-cold 10% strength hydrochloric acid and ethanol. After drying in vacuo at 100° C., 1.5 g of 1-dimethylamino-6,8-difluoro-7-(1-piperazinyl)-1,4-dihydro-4-oxo-3-quinolinecarboxylic acid hydrochloride of decomposition point 284°–286° C. are obtained.

Example 6

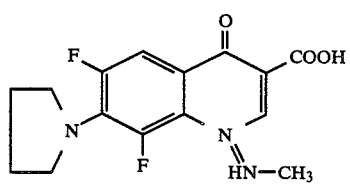

A mixture of 2.72 g of 1-methylamino-6,7,8-trifluoro-1,4-dihydro-4-oxo-3-quinolinecarboxylic acid, 2.3 g of pyrrolidine and 30 ml of pyridine is heated at the boiling point for 6 hours. The solvent is distilled off in vacuo and 20 ml of water are added to the residue. The pH is brought to 1–2 with 10% strength hydrochloric acid, while cooling with ice, and the precipitate is filtered off with suction, washed with water and dried in vacuo at 100° C. After recrystallization from glycol monomethyl ether/ethanol, 2.4 g of 1-methylamino-6,8-difluoro-7-(1-pyrrolidinyl)-1,4-dihydro-4-oxo-3-quinolinecarboxylic acid of decomposition point 282°–283° C. are obtained.

The following compounds are obtained analogously to Example 6:

Example 11

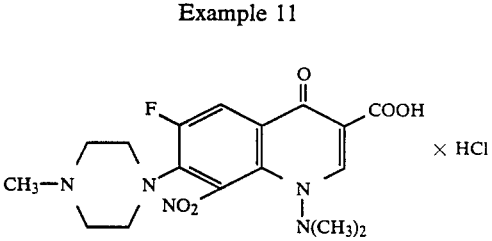

A mixture of 3.3 g of 1-dimethylamino-7-chloro-6-fluoro-8-nitro-1,4-dihydro-4-oxo-3-quinolinecarboxylic acid, 3.1 g of 1-methylpiperazine and 25 ml of dioxane is refluxed for 3 hours. The solvent is stripped off in vacuo, the residue is suspended in 25 ml of H₂O and the pH is brought to 1 with 10% strength hydrochloric acid. The precipitate is filtered off with suction in the cold and washed with a little cold 10% strength hydrochloric acid and ethanol. 3.6 g of 1-dimethylamino-6-fluoro-8-nitro-7-(4-methyl-1-piperazinyl)1,4-dihydro-4-oxo-3-quinolinecarboxylic acid hydrochloride of decomposition point 292°–294° C. are obtained.

The following compounds are obtained analogously to Example 11:

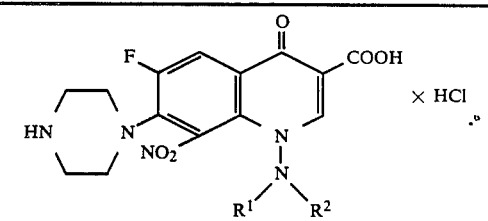

| Example | R¹ | R² | Decomposition point (°C.) |
|---------|----|----|---------------------------|
| 12 | H | CH₃ | 284 |
| 13 | CH₃ | CH₃ | 280 |

Example 14

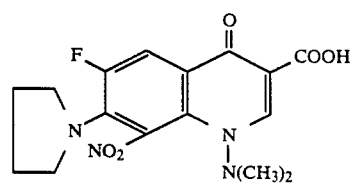

3.3 g of 1-dimethylamino-7-chloro-6-fluoro-8-nitro-1,4-dihydro-4-oxo-3-quinolinecarboxylic acid are reacted with 6 g of pyrrolidine analogously to Example 11 and, after acidification to pH 1 with 10% strength hydrochloric acid, 3.4 g of 1-dimethylamino-6-fluoro-8-nitro-7-(1-pyrrolidinyl)-1,4-dihydro-4-oxo-3-quinolinecarboxylic acid are isolated. After recrystallization from glycol monomethyl ether, the crystals have a melting point of 266°–268° C., with decomposition.

Example 15

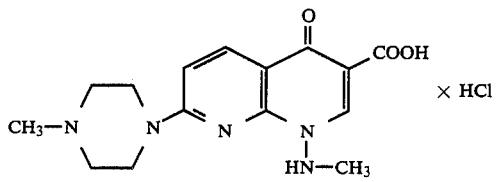

3 g of 1-methylpiperazine are added dropwise to a suspension of 2.53 g of 1-methylamino-7-chloro-1,4-dihydro-4-oxo-1,8-naphthyridine-3-carboxylic acid in 30 ml of ethanol, with stirring, the acid dissolving in a slightly exothermic reaction. The mixture is heated at the boiling point for 1 hour, the ethanol is distilled off and the reaction product is dissolved in 1N sodium hydroxide solution. The filtered solution is brought to pH 6 with 10% strength hydrochloric acid. The precipitate is filtered off in the cold, washed with a little cold water and ethanol and dried in vacuo at 80° C. 3.1 g of 1-methylamino-7-(4-methyl-1-piperazinyl)-1,4-dihydro-4-oxo-1,8-naphthyridine-3-carboxylic acid hydrochloride of decomposition point 328° C. are obtained.

The following compounds are obtained analogously to Example 15:

| Example | R¹ | R² | R³ | Decomposition point (°C.) |
|---|---|---|---|---|
| 16 | H | H | CH₃ | 316 |
| 17 | HOCH₂CH₂— | H | CH₃ | 313 |
| 18 | CH₃ | CH₃ | CH₃ | 276 (acetate) |

Example 19

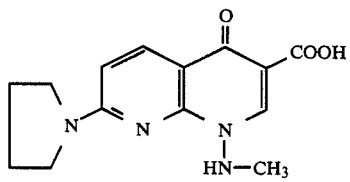

2.6 g of 1-methylamino-7-chloro-1,4-dihydro-4-oxo-1,8-naphthyridine-3-carboxylic acid are suspended in 60 ml of ethanol. 5 g of pyrrolidine are added dropwise, while cooling with ice and stirring. The mixture is then stirred at room temperature for 10 minutes and under reflux for 1 hour. The ethanol is stripped off in vacuo, the residue is dissolved in 1N sodium hydroxide solution, and the solution is filtered and acidified with 10% strength hydrochloric acid. The precipitate is filtered off with suction, washed with water and dried at 80° C. in vacuo. After recrystallization from dimethylformamide, 2.2 g of 1-methylamino-7-(1-pyrrolidinyl)-1,4-dihydro-4-oxo-1,8-naphthyridine-3-carboxylic acid of decomposition point 338°–340° C. are obtained.

The following compounds are obtained analogously to Example 19:

| Example | R¹ | R² | R³ | R⁴ | Decomposition point (°C.) |
|---|---|---|---|---|---|
| 20 | —(CH₂)₅— | | H | CH₃ | 278 |
| 21 | —(CH₂)₂O(CH₂)₂— | | H | CH₃ | 288 |

The compounds according to the invention display a broad antibacterial spectrum against Gram-positive and Gram-negative germs, in particular against Enterobacteriaceae, and in particular against those which are resistant towards various antibiotics, such as, for example, penicillins, cephalosporins, aminoglycosides, sulphonamides and tetracylines.

The compounds according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and wood, and foodstuffs and water.

The active compounds according to the invention are active against a very broad spectrum of microorganisms. With their aid, it is possible to combat Gram-negative and Gram-positive bacteria and bacteria-like microorganisms and to prevent, alleviate and/or cure diseases caused by these pathogens.

The compounds according to the invention are particularly active against bacteria and bacteria-like microorganisms. They are therefore particularly suitable in human medicine and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Micrococcaceae, such as Staphylococci, for example *Staphylococcus aureus* and *Staph. epidermidis*, (Staph.=Staphylococcus), Lactobacteriaceae, such as Streptococci, for example *Streptococcus pyogenes*, α- and β-haemolysing Streptococci, non-(γ-)-haemolysing Streptococci, Enterococci and *Dipolococcus pneumoniae* (Pneumococci) (Str.=Streptococcus); Enterobacteriaceae, such as Escherichiae bacteria of the *coli* group: Escherichia bacteria, for example *Escherichia coli*, Enterbacter bacteria, for example *E. aerogenes* and *E. cloacae*, Klebsiella bacteria, for example K-pneumoniae, Serratia, for example *Serratia marcescens* (E.=Enterobacter) (K.=Klebsiella), and Proteae bacterial of the Proteus group: Proteus, for example *Proteus vulgaris, Pr. morganii, Pr. rettgeri* and *Pr. mirabilis* (Pr.=Proteus): Pseudomonadaceae, such as Pseudomonas bacteria, for example *Pseudomonas aeruginosa,* (PS.=Pseudomonas); Bacteroidaceae, such as Bacteroides bacteria, for example *Bacteroides fragilis,* (B.=Bacteroides). Mycoplasmae, for example *Mycoplasma pneumoniae.*

The above list of pathogens is purely illustrative and is in no way to be interpreted as restrictive.

Examples which may be mentioned of diseases which can be prevented, alleviated and/or cured by the compounds according to the invention are: diseases of the respiratory tract and the pharyngial cavity; otitis; pharyngitis; pneumonia, peritonitis; pyelonephritis; cystisis; endocarditis; systemic infections; bronchitis; arthritis; local infections and septic diseases.

The present invention includes pharmaceutical formulations which, in addition to non-toxic, inert pharmaceutically suitable excipients, contain one or more compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound correspond to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is given in one administration, and which usually corresponds to a whole, a half, one third or one quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions pastes, ointments, gels, creams, lotions, powders and sprays may be mentioned as preferred pharmaceutical formulations.

Tablets, dragees, capsules, pills and granules can contain the active compound or compounds alongside the customary excipients, they (a) fillers and extenders, for example starches, lactose, sucrose, glucose, manitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talcs, silica, aluminum hydroxide, calcium silicate and polyamide powders, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, and suspending agents, for example ethoxylated isostearyl alcohol, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95,% by weight of the total mixture.

The abovementioned pharmaceutical formulations can also contain other pharmaceutical active compounds, in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100 mg/kg of body weight every 24 hours, optionally in the form of several individual administrations, in order to achieve the desired results. An individual administration preferably contains the active compound or compounds according to the invention in amounts of about 1 to about 250, in particular 3 to 60 mg/kg of body weight. However, it may be necessary to deviate from the dosages mentioned, and in particular to do so as a function of the species and the body weight of the subject to be treated, the nature and severity of the disease, the nature of the formulation and of the administration of the medicament and the period or interval over which the administration takes place. Thus it can in some cases suffice to manage with less than the abovementioned amount of active compound, while in other cases the abovementioned amount of active compound must be exceeded. The particular optimum dosage required and the type of administration of the active compounds can easily be determined by any one skilled in the art, on the basis of his expert knowledge.

The new compounds can be administered in the customary concentrations and formulations together with the feed or with feed formulations or with the drinking water. By this means, it is possible to prevent, alleviate and/or cure an infection by Gram-negative or Gram-positive bacteria and thereby to achieve promotion of growth and better utilisation of the feed.

1,7-Diamino-6-fluoroquinolone-3-carboxylic acids are indeed already known from European Patent Application No. 0,090,424. However, the new 1,7-diamino-1,4-dihydro-4-oxo-3-quinolinecarboxylic acids according to the invention are superior to these known compounds in respect of their antibacterial action and the serum levels which can be achieved, as can be seen from the following Tables 1, 2 and 3.

Table 1 shows MIC values of the compound according to the invention in Example 3 (I), in comparison with the analogous 6-monofluoro derivative (II) known from EP-AS (European Published Specification) No. 0,090,424. In most cases the values are identical, but for some strains they are about 2-4 times better. In studies on the pharmacokinetics in mice following oral and parenteral administration (see Tables 2+3) it was possible to demonstrate that Example 3 (I) produces higher serum levels than the comparison product. With about the same in vitro activity, a higher probability of therapeutic action exists in vivo as a result of the better bioavailability following oral and parenteral administration.

TABLE 1

| Strain | MIC mcg/ml | |
|---|---|---|
| | II | I |
| E. coli 455/7 | 8 | 8 |
| E. coli A 261 | 0.06 | 0.06 |
| Klebsiella 6179 | 0.25 | 0.125 |
| Klebsiella 57 USA | 0.25 | 0.125 |
| Proteus mir. 8223 | 4 | 4 |
| Proteus mir. 8175 | 0.125 | 0.25 |
| Providencia 12052 | 16 | 4 |
| Pseudomonas W. | 1 | 1 |

Agar dilution test/Isosensitest medium

TABLE 2

Serum levels in mice after oral administration of 5 mg/kg

| Product | mcg/ml of serum | | | |
|---|---|---|---|---|
| | 15' | 30' | 1 hour | 2 hours |
| I | 0.9 | 1.2 | 0.6 | 0.25 |
| II | 0 7 | 0.58 | 0.32 | 0.1 |

TABLE 3

Serum levels in mice following subcutaneous administration of 5 mg/kg

| Product | mcg/ml of serum | | | |
|---|---|---|---|---|
| | 15' | 30' | 1 hour | 2 hours |
| I | 1.2 | 1.4 | 0.92 | 0.3 |
| II | 0.84 | 1.3 | 0.45 | 0.1 |

It will be understood that the specification and examples are illustrative but not limitative of the present invention and that other embodiments within the spirit and scope of the invention will suggest themselves to those skilled in the art.

We claim:

1. A 1,7-diamino-1,4-dihydro-4-oxo-3-(aza)-quinolinecarboxylic acid of the formula

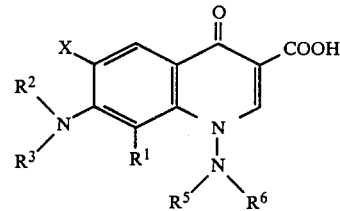

in which
$R^1$ is halogen,
$R^2$ and $R^3$ each independently is $C_1$–$C_3$-alkyl, or together with the nitrogen atom to which they are bonded, form a pyrrolidine, piperidine, piperazine or morpholine ring, which can optionally be mono-, di- or tri-substituted on the carbon atoms by $C_1$–$C_3$-alkyl, hydroxyl, alkoxy with 1-3 carbon atoms, amino, methylamino or ethylamino, it being possible for a carbon atom in each case to carry only one substituent,
$R^4$ is hydrogen, an alkyl or alkenyl group which has 1 to 4 carbon atoms and is optionally substituted by a hydroxyl, alkoxy, alkylmercapto, alkylamino or dialkylamino group with 1 to 3 carbon atoms per alkyl radical, the cyano group or an alkoxycarbonyl group with 1 to 4 carbon atoms in the alcohol part, or a benzyloxycarbonyl group, a phenylalkyl group which has up to 4 carbon atoms in the aliphatic part and is optionally substituted in the phenyl radical, a phenyl radical which is optionally monosubstituted or disubstituted by hydroxyl, methoxy, chlorine and fluorine, a phenylcarboxylic acid acyl radical which is optionally monosubstituted or disubstituted by hydroxyl, methoxy, chlorine or fluorine, an oxoalkyl radical with up to 6 carbon atoms or a cycloalkyl-alkyl radical which has up to 6 carbon atoms in the cyclic part and up to 3 carbon atoms in the acyclic part,
$R^5$ and $R^6$ each independently is hydrogen or an alkyl group with 1 to 4 carbon atoms, and X is hydrogen, a nitro group or halogen,
or a pharmaceutically acceptable salt thereof.

2. A 1,7-diamino-1,4-dihydro-4-oxo-3-(aza)-quinolinecarboxylic acid or salt according to claim 1, in which
X is halogen.

3. A 1,7-diamino-1,4-dihydro-4-oxo-3-(aza)-quinolinecarboxylic acid or salt according to claim 1, in which
$R^2$ and $R^3$ each independently is $C_1$–$C_3$-alkyl, or together with the nitrogen atom to which they are bonded form a pyrrolidine, piperidine, piperazine or morpholine ring.

4. A 1,7-diamino-1,4-dihydro-4-oxo-3-(aza)-quinolinecarboxylic acid or salt according to claim 1, in which

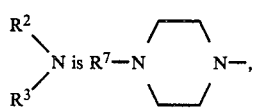

and
$R^7$ is hydrogen or an alkyl group with 1 to 4 carbon atoms.

5. A compound according to claim 1, wherein such compound is 1-methylamino-6,8-difluoro-7-(1-piperazinyl)-1,4-1,4-dihydro-4-oxo-3-quinolinecarboxylic acid of the formula

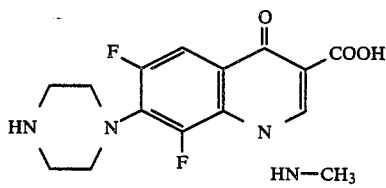

or a pharmaceutically acceptable salt thereof.

6. A compound according to claim 1, wherein such compound is 1-methylamino-6,8-difluoro-7-(4-methylpiperazinyl)-1,4-dihydro-4-oxo-3-quinolinecarboxylic acid of the formula

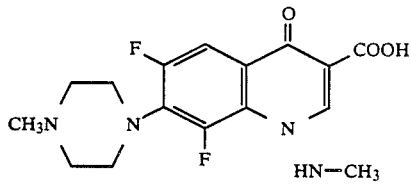

or a pharmaceutically acceptable salt thereof.

7. A compound according to claim 1, wherein such compound is 1-methylamino-6,8-difluoro-7-(1-pyrrolidinyl)-1,4-dihydro-4-oxo-3-quinolinecarboxylic acid of the formula

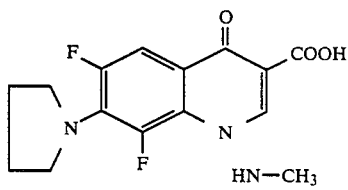

or a pharmaceutically acceptable salt thereof.

8. An antibacterial composition comprising an antibacterially effective amount of a compound or salt according to claim 1 in admixture with a diluent.

9. A unit dose of a composition according to claim 8 in the form of a tablet, capsule or ampule.

10. A method of combating bacteria which comprises applying to such bacteria or to a bacteria habitat an antibacterially effective amount of a compound or salt according to claim 1.

11. The method according to claim 10, wherein such compound is
1-methylamino-6,8-difluoro-7-(1-piperazinyl)-1,4-1,4-dihydro-4-oxo-3-quinolinecarboxylic acid,
1-methylamino-6,8-difluoro-7-(4-methylpiperazinyl)-1,4-dihydro-4-oxo-3-quinolinecarboxylic acid,
1-methylamino-6,8-difluoro-7-(1-pyrrolidinyl)-1,4-dihydro-4-oxo-3-quinolinecarboxylic acid,
or a pharmaceutically acceptable salt thereof.

* * * * *

UNITED STATES PATENT AND TRADEMARK OFFICE
CERTIFICATE OF CORRECTION

PATENT NO. : 4,753,925

DATED : June 28, 1988

INVENTOR(S) : Klaus Grohe, et al

It is certified that error appears in the above-identified patent and that said Letters Patent is hereby corrected as shown below:

| | |
|---|---|
| Col. 6, line 7 | Delete "82°-84°" and substitute --82°-85°-- |
| Col. 6, line 63 | Correct spelling of -- -quinoline-carboxylic" |
| Col. 7, line 51 | Delete "...hydrazino)acrylate" and substitute --...hydrazino)-acrylate-- |
| Col. 8, line 36 | Delete "ice-wter" and substitute --ice-water-- |
| Col. 12, line 38 | Delete "-piperazinyl)1,4-" and substitute -- -piperazinyl)-1,4- -- |
| Col. 18, line 8 | Delete "0 7" and substitute --0.7-- |

Signed and Sealed this

Twenty-third Day of May, 1989

Attest:

DONALD J. QUIGG

Attesting Officer

Commissioner of Patents and Trademarks